US008437839B2

(12) United States Patent
Lux

(10) Patent No.: US 8,437,839 B2
(45) Date of Patent: May 7, 2013

(54) ELECTROCARDIOGRAPHIC ASSESSMENT OF ARRHYTHMIA RISK

(75) Inventor: Robert L. Lux, Park City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 21 days.

(21) Appl. No.: 13/085,444

(22) Filed: Apr. 12, 2011

(65) Prior Publication Data

US 2012/0265086 A1 Oct. 18, 2012

(51) Int. Cl.
*A61B 5/04* (2006.01)

(52) U.S. Cl.
USPC .......................................................... 600/515

(58) Field of Classification Search .................... 600/515
See application file for complete search history.

(56) References Cited

U.S. PATENT DOCUMENTS

| 5,609,158 | A | 3/1997 | Chan |
| 6,304,773 | B1 * | 10/2001 | Taylor et al. ................. 600/515 |
| 7,593,766 | B2 * | 9/2009 | Faber et al. .................. 600/518 |
| 2004/0243014 | A1 * | 12/2004 | Lee et al. ..................... 600/510 |
| 2008/0065162 | A1 | 3/2008 | Pittaro |
| 2010/0217144 | A1 | 8/2010 | Brian |
| 2011/0054335 | A1 | 3/2011 | Zhang |

OTHER PUBLICATIONS

Das et al., "Fragmented Wide QRS on a 12-Lead ECG: A Sign of Myocardial Scar and Poor Prognosis", Circulation: Arrhythmia and Electrophysiology—Journal of the American Heart Association, 2008, pp. 258-268, vol. 1.

Censi et al., "Morphological analysis of P-wave in patients prone to atrial fibrillation", Engineering in Medicine and Biology Society, EMBS '06, 28th Annual International Conference of the IEEE, Aug. 30, 2006—Sep. 3, 2006, pp. 4020-4023.

Chandy et al., "Increases in P-Wave Dispersion Predict Postoperative Atrial Fibrillation After Coronary Artery Bypass Graft Surgery", Anesthesia & Analgesia, Feb. 2004, pp. 303-310, vol. 98, No. 2.

Dilaveris et al., "P-Wave Duration and Dispersion Analysis: Methodological Considerations—Response", Circulation: Journal of the American Heart Association, 2001, vol. 103, p. e111.

Kalifa et al., "Mechanisms of Wave Fractionation at Boundaries of High-Frequency Excitation in the Posterior Left Atrium of the Isolated Sheep Heart During Atrial Fibrillation", Circulation: Journal of the American Heart Association, 2006, pp. 626-633, vol. 113.

International Search Report and Written Opinion for International Application No. PCT/US2012/033156, mailed Oct. 30, 2012, in 8 pages.

* cited by examiner

*Primary Examiner* — Christopher D Koharski
*Assistant Examiner* — Philip Edwards
(74) *Attorney, Agent, or Firm* — James W. Hill; McDermott Will & Emery LLP

(57) ABSTRACT

Systems and methods are provided in the disclosure for estimating a risk of arrhythmia in a patient using electrocardiographic analysis. In certain aspects, a method of estimating a risk of arrhythmia in a patient is provided. The method comprises receiving electrocardiographic signals of the patient from a plurality of leads over a plurality of heart beats, averaging the electrocardiographic signals to produce an averaged electrocardiographic signal, and determining deflections in the averaged electrocardiographic signal, wherein each deflection has an amplitude and a duration. The method further comprises determining a significance of each deflection based on whether the amplitude of that deflection exceeds a threshold, and estimating a risk of arrhythmia in the patient based on at least one of a number, the amplitudes, and the durations of the significant deflections within a portion of the averaged electrocardiographic signal.

23 Claims, 10 Drawing Sheets

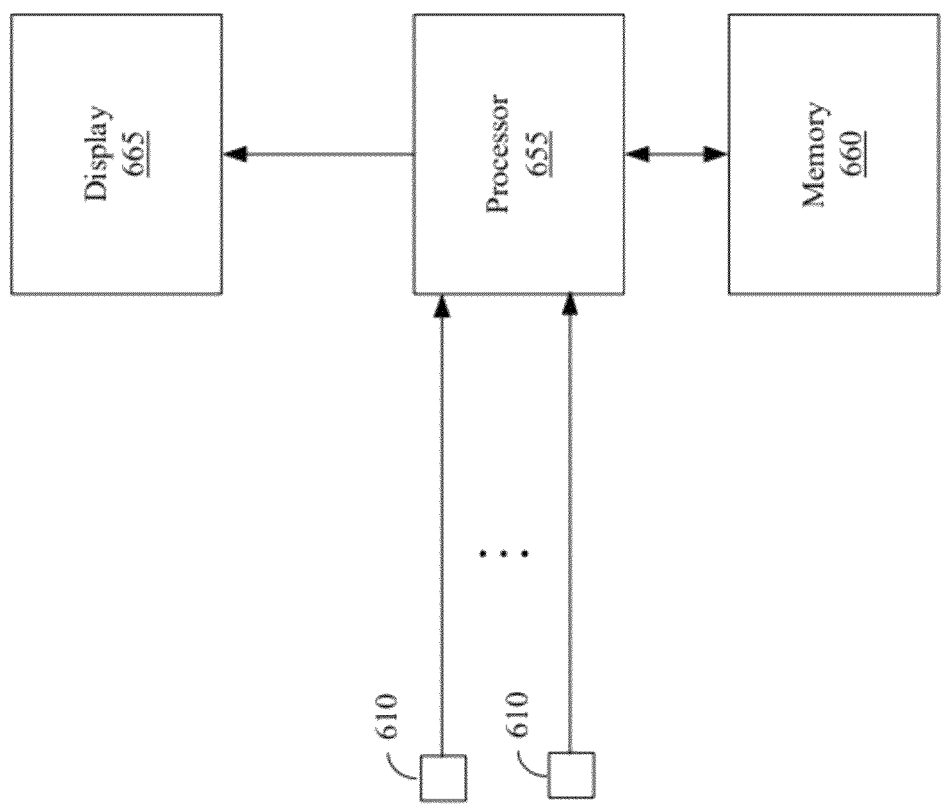

ELECTROCARDIOGRAPHIC ASSESSMENT OF ARRHYTHMIA RISK

FIELD

The disclosure relates generally to systems and methods for electrocardiographic analysis.

BACKGROUND

Atrial fibrillation (AF) is a common arrhythmia with increasing incidence with age and presence of heart disease. If left untreated in a patient, the risk of stroke, heart attack and heart failure is very high, and after treatment, risk still remains high. Several known causes of increased risk of AF are the functional, structural, and electrical changes in the heart that come with age and the presence of heart disease (myocardial infarction, cardiomyopathy, hypertrophy, congestive heart failure, etc.). These changes result in abnormal conduction of electrical impulses in the heart.

SUMMARY

Systems and methods are provided in the disclosure for estimating a risk of arrhythmia in a patient using electrocardiographic analysis.

In certain aspects, a method of estimating a risk of arrhythmia in a patient is provided. The method comprises receiving electrocardiographic signals of the patient over a plurality of heart beats, averaging the electrocardiographic signals to produce an averaged electrocardiographic signal, and determining deflections in the averaged electrocardiographic signal, wherein each deflection has an amplitude and a duration. The method further comprises determining a significance of each deflection based on whether the amplitude of that deflection exceeds a threshold, and estimating a risk of arrhythmia in the patient based on at least one of a number, the amplitudes, and the durations of the significant deflections within a portion of the averaged electrocardiographic signal.

In certain aspects, each beat may be detected by, e.g., the QRS, and the beats may be time aligned to the P wave or QRS In certain aspects, the estimating is based on at least two of the number, the amplitudes, and the durations of the significant deflections within the portion.

In certain aspects, the estimating is based on the number, the amplitudes, and the durations of the significant deflections within the portion.

In certain aspects, the portion comprises a P wave of the averaged electrocardiographic signal.

In certain aspects, the portion consists essentially of a P wave of the averaged electrocardiographic signal.

In certain aspects, the estimating comprises comparing a number, a mean amplitude, and a mean duration of the significant deflections of the patient to a respective number, a respective mean amplitude, and a respective mean duration of significant deflections of at least one normal subject, and estimating a risk of atrial fibrillation in the patient based on the comparison.

In certain aspects, the portion of the averaged electrocardiographic signal comprises a QRS complex, and the estimating comprises estimating a risk of ventricular arrhythmia of the patient.

In certain aspects, the estimating comprises comparing at least one of a number, a mean amplitude and a mean duration of the significant deflections of the patient to at least one of a respective number, a respective mean amplitude, and a respective mean duration of significant deflections of at least one normal subject, and estimating a risk of at least one of ventricular tachycardia and ventricular fibrillation in the patient based on the comparison.

In certain aspects, the threshold comprises a factor times the maximum deflection amplitude in at least one of a T-P, a P-R, and an S-T segment of the averaged electrocardiographic signal.

In certain aspects, the determining deflections in the averaged electrocardiographic signal comprises determining extrema in the averaged electrocardiographic signal, and defining each deflection as a line segment between adjacent extrema.

In certain aspects, the estimating is based on a mean amplitude of the significant deflections.

In certain aspects, the estimating is based on a mean duration of the significant deflections.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

General descriptions provided herein that implement various features of the disclosure will now be described with reference to the drawings. The drawings and the associated descriptions are provided to illustrate embodiments of the disclosure and not to limit the scope of the disclosure.

FIG. 6 is a conceptual block diagram of a system for obtaining and processing electrocardiographic signals of a patient to assess cardiac conduction and the patient's risk for arrhythmia according to an embodiment of the subject technology.

DETAILED DESCRIPTION

The subject technology involves estimating risk of ventricular or atrial arrhythmias based on electrocardiographic analysis. One such arrhythmia is atrial fibrillation (AF), a clinically significant arrhythmia leading to an increased risk of stroke and myocardial infarction. An underlying factor contributing to increased risk of developing AF is age and/or disease dependent fibrosis that alters normal conduction in the heart, sometimes resulting in P wave fractionation (PF) observed in electrograms recorded directly from the atria during electrophysiologic study, which is a likely marker of discontinuous conduction in the atria. In one embodiment of the subject technology, high resolution, signal averaged P waves from body surface ECGs are analyzed to quantify P wave fractionation and provide a useful index for predicting AF risk and assessing conduction abnormalities.

Currently, there are no simple, non-invasive, inexpensive means for assessing atrial or ventricular fibrosis, a substrate for increased risk of arrhythmias. As discussed further below, in one embodiment of the subject technology, quantitative analysis of high resolution signal averaged P waves of the ECG (SAECG-P) can provide estimates of atrial (and ventricular) conduction abnormalities associated with discontinuous conduction, which is an established, significant contributing factor for atrial and ventricular arrhythmias.

A methodology for quantifying fractionation of electrocardiographic P waves (atrial depolarization) or QRS complexes (ventricular depolarization) according to various embodiments of the subject technology is described below.

Signals to be Analyzed and Assessed

Any body surface signals are appropriate for analysis, including conventional 12-lead ECG signals (Leads I, II, and $V_1$-$V_6$), vectorcardiogram leads, or body surface mapping leads (arbitrary number). Given that body surface fractionation waveforms are a reflection of underlying and directly measured atrial or ventricular electrograms showing fractionation, leads in close proximity to the heart (e.g., chest leads) are more likely to show fractionation than distant leads such as the limb leads (I, II, II).

Figure 1:
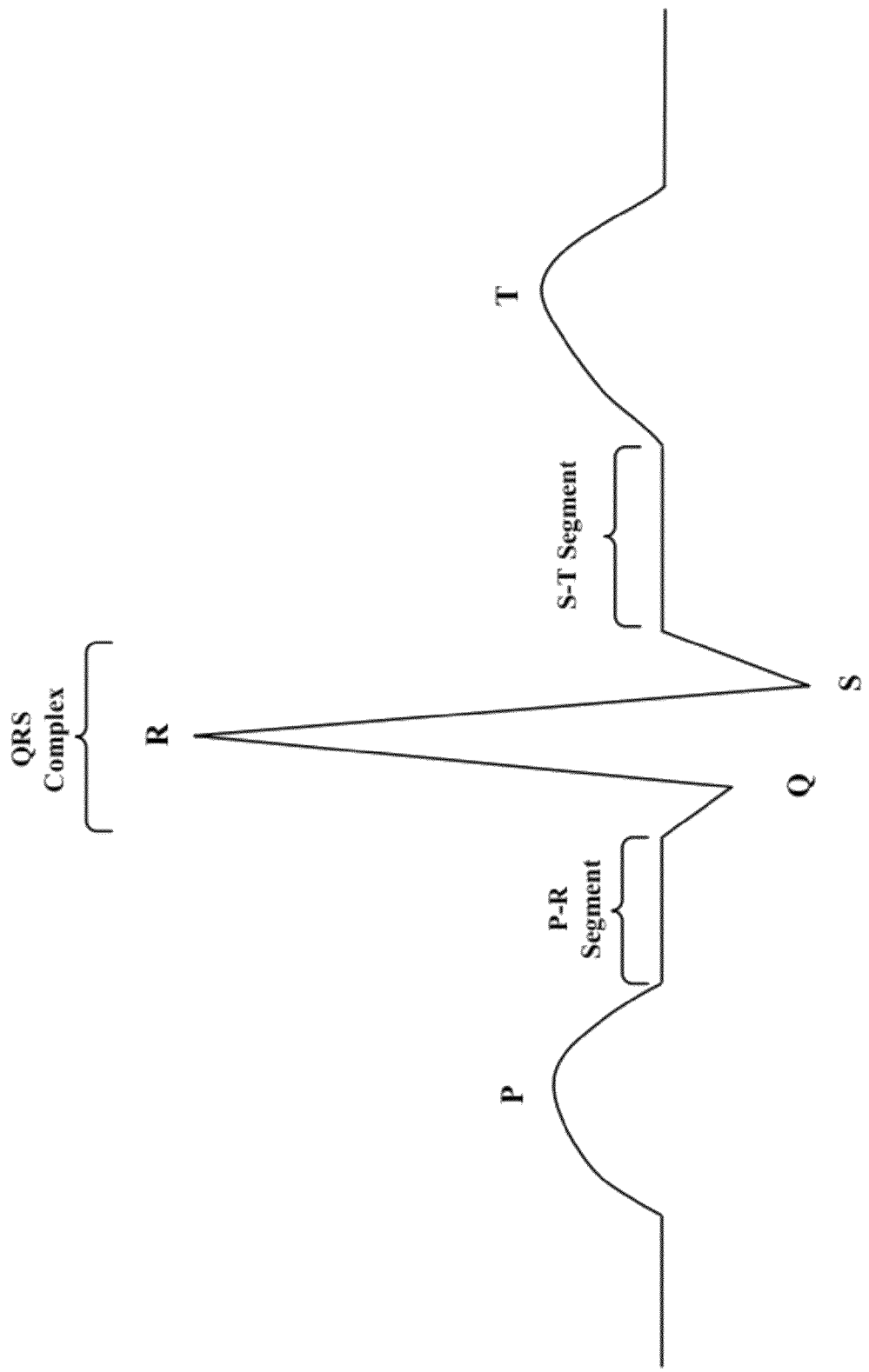
FIG. 1 shows an example of an electrocardiogram including P, Q, R, S and T waves.

FIG. 1 shows a simplified example of an electrogram for one heart beat. In this example, the electrogram includes P, Q, R, S and T waves. The P wave represents atrial depolarization, which originates at the sinoatrial (SA) node and propagates through conductive tissue in the artia, causing the heart muscles of the atria to contract. The Q, R and S waves form a QRS complex, which represents ventricular depolarization that propagates through conductive tissue in the ventricles. The ventricular depolarization is typically delayed by 120 milliseconds to 200 milliseconds by the atrioventricular (AV) node, which electrically connects the conductive tissue of the ventricles with the conductive tissue of the atria. In FIG. 1, the delay is manifested as the P-R segment between the P wave and the QRS complex. The T wave following the QRS complex represents repolarization of the ventricles and is separated from the QRS complex by the S-T segment.

Signal Averaging with Time Alignment

A purpose of signal averaging is to reduce incoherent, random noise from the recorded signals while enhancing or revealing the synchronized (phase locked) and stationary signal component that reflects the underlying electrophysiology. In essence, by increasing signal to noise ratio (SNR), one can reveal very important signal signatures phase locked (synchronized) to a repetitive trigger but that are embedded in incoherent (random) noise many times larger. The repetitive trigger may be regular heart beats, photo flashes, audio clicks, etc. and the signals may be cardiac (ECG), muscle (EMG), or neural (EEG).

For ECG, the signals may be digitally sampled electrocardiograms recorded from an arbitrary number of body surface electrodes, often called leads. To implement signal averaging, each heart beat is detected, typically by identifying the large amplitude QRS complex or by finding the time of the minimum derivative of the signal within a particular window of samples. Once all beats are identified, the electrocardiograms, time aligned to the QRS, of all the beats in the recording can be "stacked" and averaged.

Mathematically, let $s_i(k)$ be the $i^{th}$ of M ECG signals, where each ECG signal corresponds to one heart beat, and let $n_i(k)$ be additive random noise, both with samples k=1,N. The recorded signal $e_i(k)$ is given by $$e_i(k)=s_i(k)+n_i(k) \text{ for } i=1,M \text{ and } k=1,N \quad (1)$$

The average of the M signals is given by:

$$\bar{e}(k)=\bar{s}(k)+\bar{n}(k) \quad (2)$$

where $$\bar{s}(k) = \frac{1}{M}\sum_{i=1}^{M} s_i(k) \quad (3)$$

and $$\bar{n}(k) = \frac{1}{M}\sum_{i=1}^{M} n_i(k) \quad (4)$$

Since the noise is random, $$\lim_{M \to \infty} \bar{n}(k) \to 0 \quad (5)$$

which, for large M, results in:

$$\bar{e}(k) \approx \bar{s}(k) \quad (6)$$

Thus, by averaging a large number of ECG signals corresponding to a large number of heart beats, the additive random noise can be removed.

Implicit in signal averaging is that each epoch (beat) to be averaged must be aligned so that specific samples of each epoch correspond to those in all other epochs, e.g., the R wave peaks of all beats align, or the onsets of all P waves align, etc. In order to ensure accurate alignment, cross correlation techniques can be used in which the P wave or QRS complex of an individual beat is shifted over a range of samples in order to achieve a maximum correlation with a P wave or QRS complex of a "template beat."

Examples of SAECG-P.

Figure 2A:
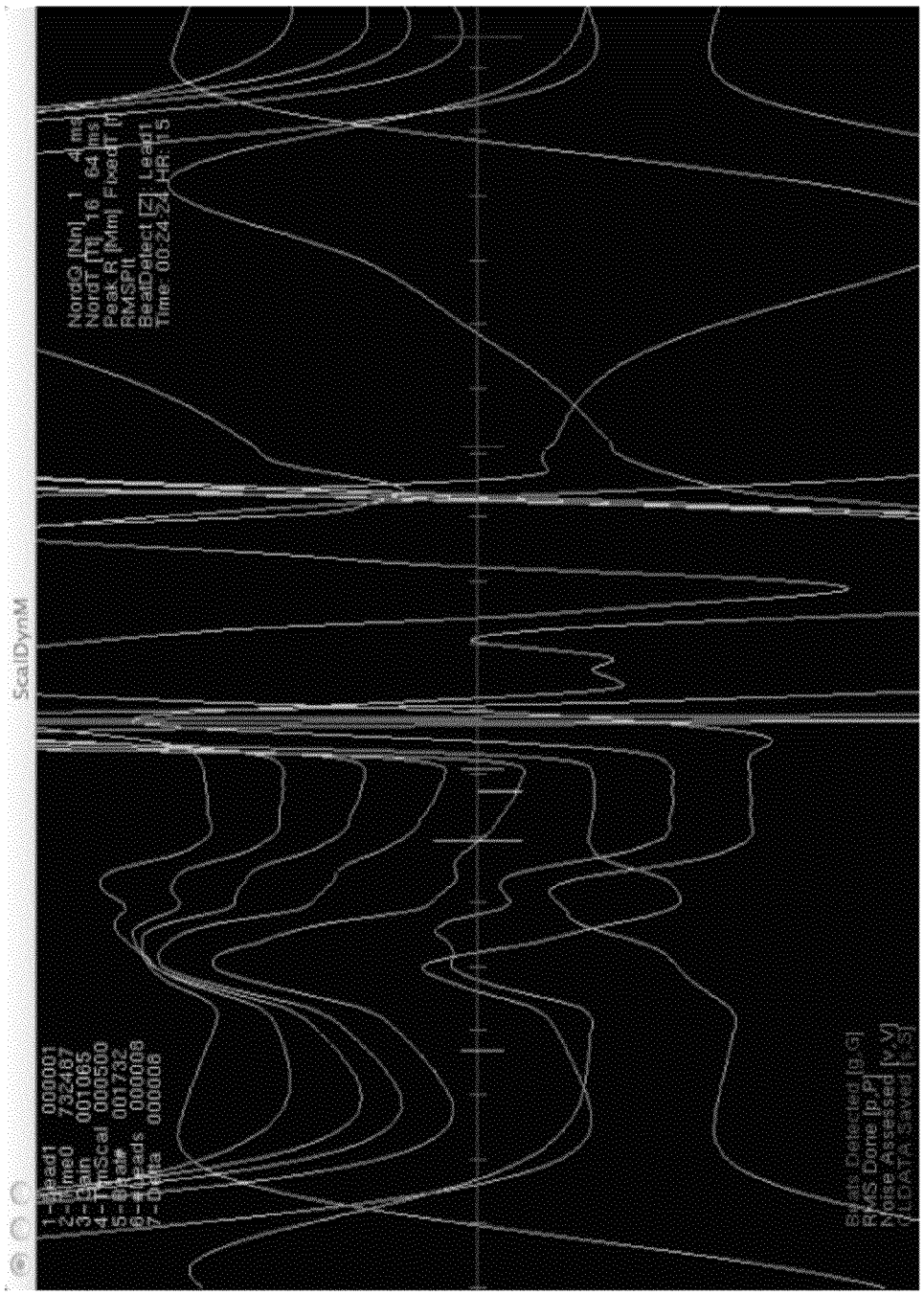
FIG. 2A shows signal averaged P waves determined from 300 time-aligned P waves for a normal healthy subject.

Since an objective of this technology is to detect small abnormal variation in the signal averaged waveforms, it is important to visualize these inflections before quantifying them. FIG. 2A shows signal averaged P waves from a young healthy subject taken from ECG Leads I, II and V1-V6. Each signal averaged P wave is averaged from 300 time-aligned P waves. As shown in FIG. 2A, for the young healthy subject, the signal averaged P waves are smooth.

Figure 2B:
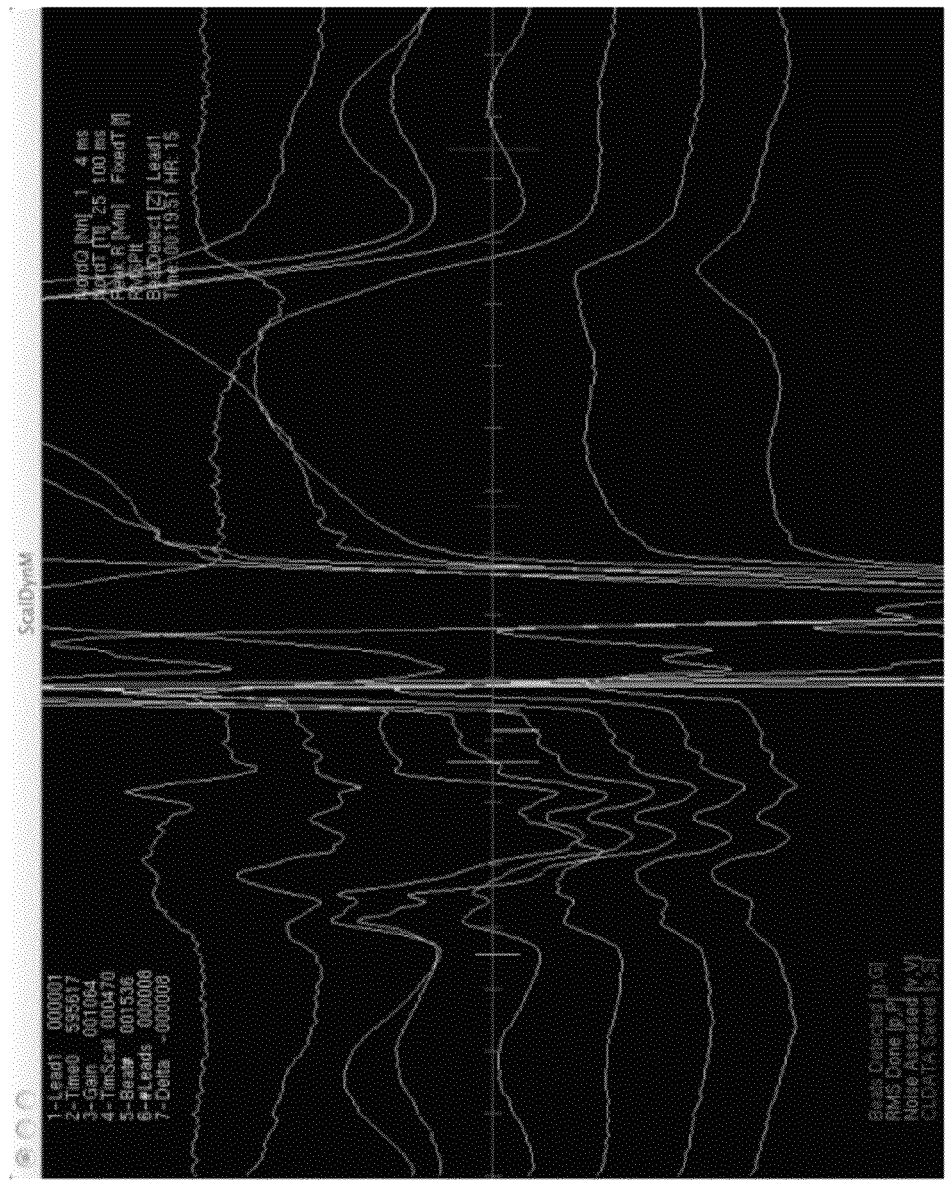
FIG. 2B shows signal averaged P waves determined from 300 time-aligned P waves for a patient suffering from advanced coronary disease.

FIG. 2B shows signal averaged P waves from an elderly patient with severe coronary artery disease taken from ECG Leads I, II and V1-V6. Each signal averaged P wave is averaged from 300 time-aligned P waves. As shown in FIG. 2B, for the elderly patient with severe coronary artery disease, the signal averaged P waves have a high frequency, jagged nature. Note that the waveforms preceding the P waves (T-P segments) in both figures are smooth with no apparent variation.

The objective of the following analysis will be to characterize and quantify the excursions of these signals, whether normal or abnormal.

Identification of Local Extrema and "Deflections" in Signal Averaged ECGs.

As defined above, each signal averaged ECG comprises a sequence of samples:

$$\{\bar{s}(k):k=1,N\} \quad (7)$$

The extrema (singular extremum) of $\bar{s}(k)$ comprise the local maxima and the local minima. Each exremum may be defined as a sample for which both adjacent samples are either larger or smaller than the sample. Thus, a local maximum, $Lmax_j$, occurs at sample r if:

$$\bar{s}(r-1)<\bar{s}(r)>\bar{s}(r+1) \quad (8)$$

and is defined as:

$$Lmax_j = \bar{s}(r_j) \quad (9)$$

A local minimum, $Lmax_j$, occurs at sample p if:

$$\bar{s}(p-1)>\bar{s}(p)<\bar{s}(p+1) \quad (10)$$

and is defined as $$Lmin_j = \bar{s}(p_j) \quad (11)$$

Figure 3A:
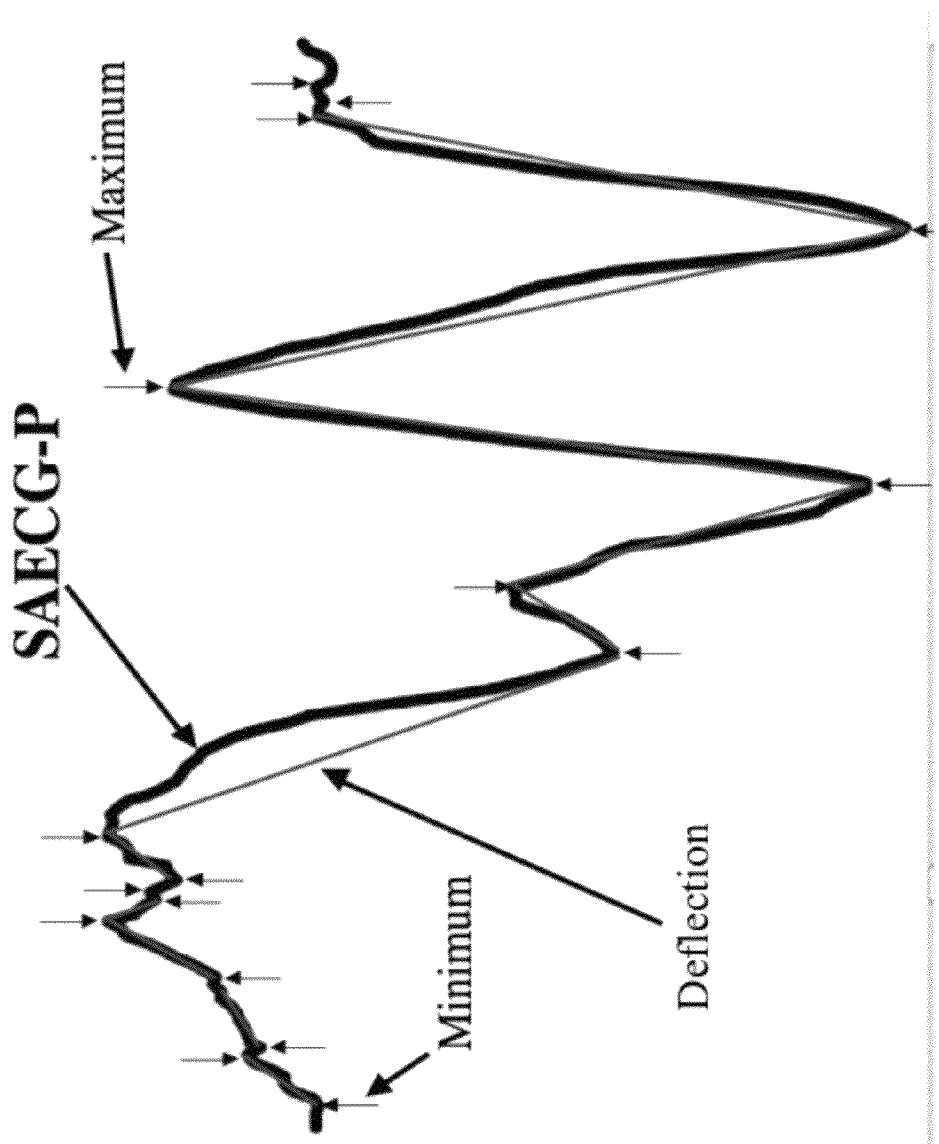
FIG. 3A shows an example of a signal averaged P wave with local minima, local maxima and deflections.
Figure 3B:
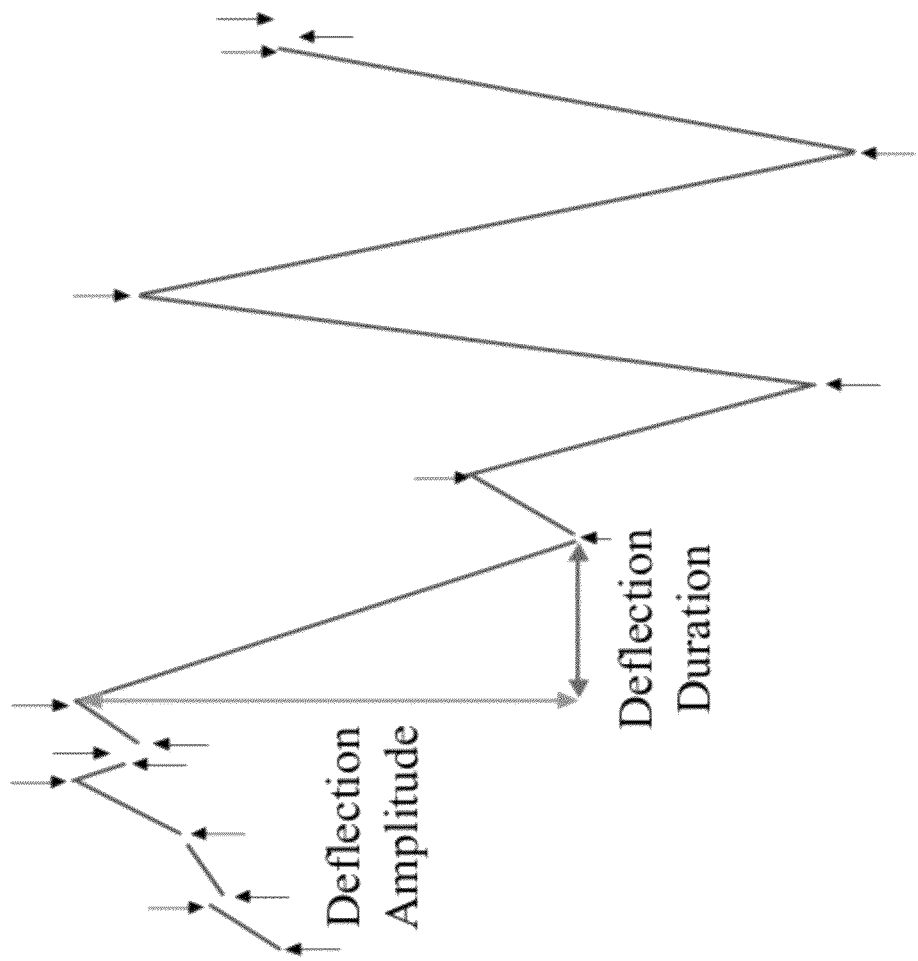
FIG. 3B shows the deflections of the signal averaged P wave in FIG. 3A.

In one embodiment, a "deflection", D, is defined as a line between adjacent extrema, either a local maximum to a local minimum or visa versa. Each deflection is characterized by an amplitude, $D_A$, component and a time duration, $D_D$, component specified as the amplitude and time difference between the adjacent local extrema, respectively. FIG. 3A shows an example of a signal segment having multiple local maxima and minima. In FIG. 3A, each local maximum is represented by a down arrow and each local minimum is represented by an up arrow. Also shown in FIG. 3A are the corresponding deflections, where each deflection is shown as a line segment between a local maximum and a local minimum or vice versa. FIG. 3B shows the deflections of FIG. 3A isolated from the signal. FIG. 3B also shows an example of the amplitude component and duration component of one of the deflections.

After the deflections are determined in a SAECG, "significant" deflections may be identified for further analysis while insignificant deflections may be discarded. A significant deflection may be defined as a deflection that is equal to or exceeds a deflection amplitude threshold. The deflection threshold can be established in one of several ways. In one embodiment, a specific amplitude, e.g., 2 µV, can be specified for the deflection threshold. In another embodiment, the deflection threshold can be set as some factor (e.g., 1.5) times the maximum deflection in the T-P, P-R, or S-T segment of the SAECG where there are no depolarizations. The latter approach is attractive from the standpoint that the Signal-to-Noise Ratio (SNR) is different for each lead and hence the significance of deflections is measured in terms of the noise in each lead.

Finally, deflection statistics (e.g., number of significant deflections, mean deflection amplitude and mean deflection duration) can be tabulated for each lead and for all leads for a patient and compared to values in normal healthy subjects to assess the patient's risk for arrhythmia.

Figure 4A:
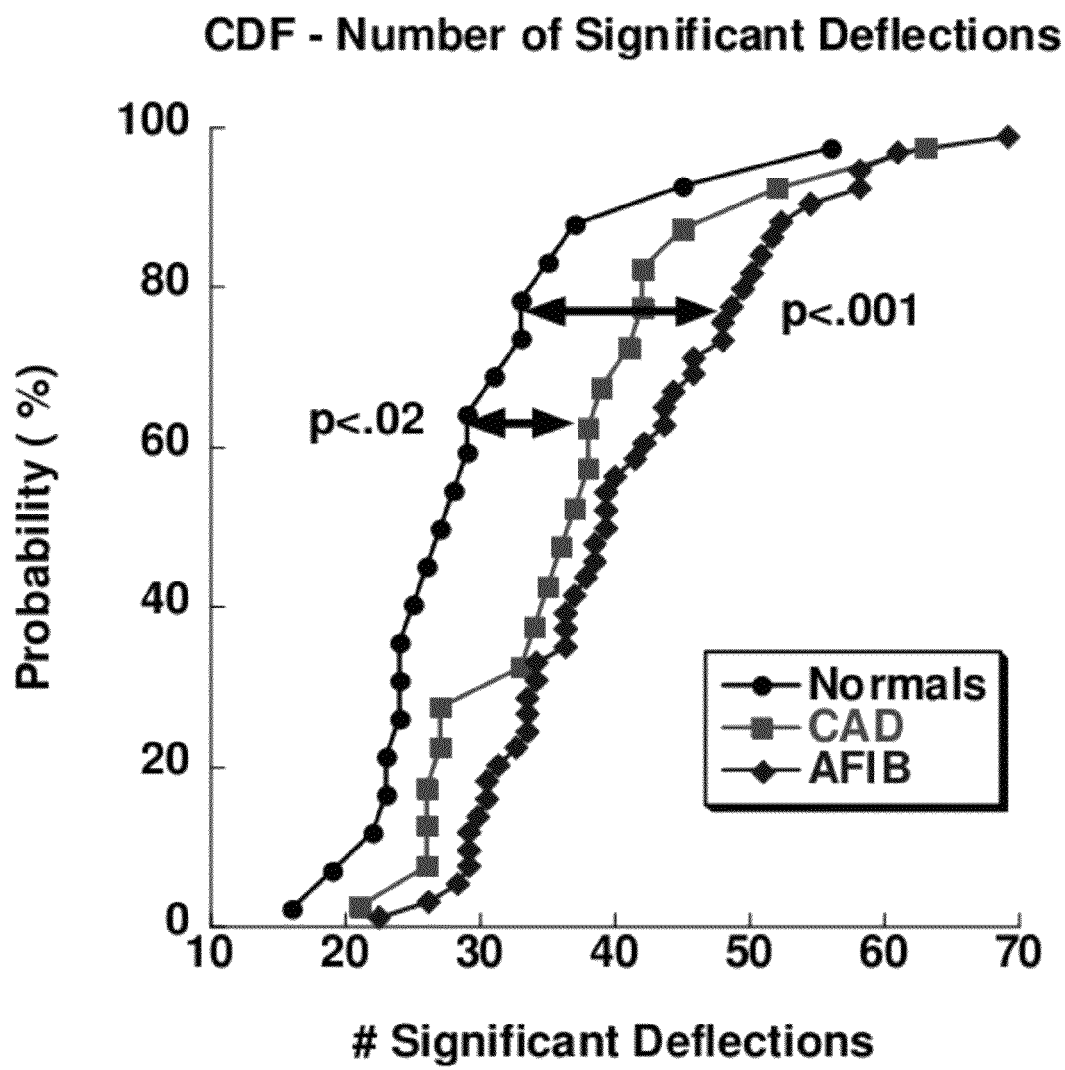
FIG. 4A shows cumulative distribution functions for number of significant deflection for three groups of subjects: normal subjects, subjects with coronary disease, and subjects with atrial fibrillation.

FIG. 4A shows cumulative distribution functions for number of significant deflections for three groups of subjects: normal subjects (no heart disease), subjects with documented coronary artery disease (CAD), some with myocardial infarctions, and generally older than the normal subjects, and subjects with previous episodes of atrial fibrillation, with recordings taken in sinus rhythm (AFIB in FIG. 4A). In this example, the number of significant deflections for each group was determined for P waves.

In FIG. 4A, the cumulative distribution function for each group of subjects shows the percentage of subjects in that group having a number of significant deflections equal to or less than a given number of significant deflections on the horizontal axis. As shown in FIG. 4A, the subjects with coronary artery disease tend to have a larger number of significant deflections than the normal subjects, and the subjects with atrial fibrillation tend to have an even larger number of significant deflections than the normal subjects. This is to be expected, since the high frequency, jagged nature of the signal averaged ECG for a subject with coronary artery disease tends to produce a large number of small deflections, as shown in the example in FIG. 2B. In contrast, the smooth nature of the signal averaged ECG for a normal subject tends to produce a small number of large deflections, as shown in the example in FIG. 2A.

A Kolmogorov-Smirnov test was performed on the cumulative distribution functions in FIG. 4A. In FIG. 4A, the p-value between the cumulative distribution functions for the subjects with coronary artery disease and the normal subjects was less than 0.02, indicating that the difference in the cumulative distribution functions was due to the underlying discontinuous conduction in subjects with coronary artery disease rather than due to chance. The p-value between the cumulative distribution functions for the subjects with atrial fibrillation and the normal subjects was less than 0.001 indicating that the difference was highly significant.

Figure 4B:
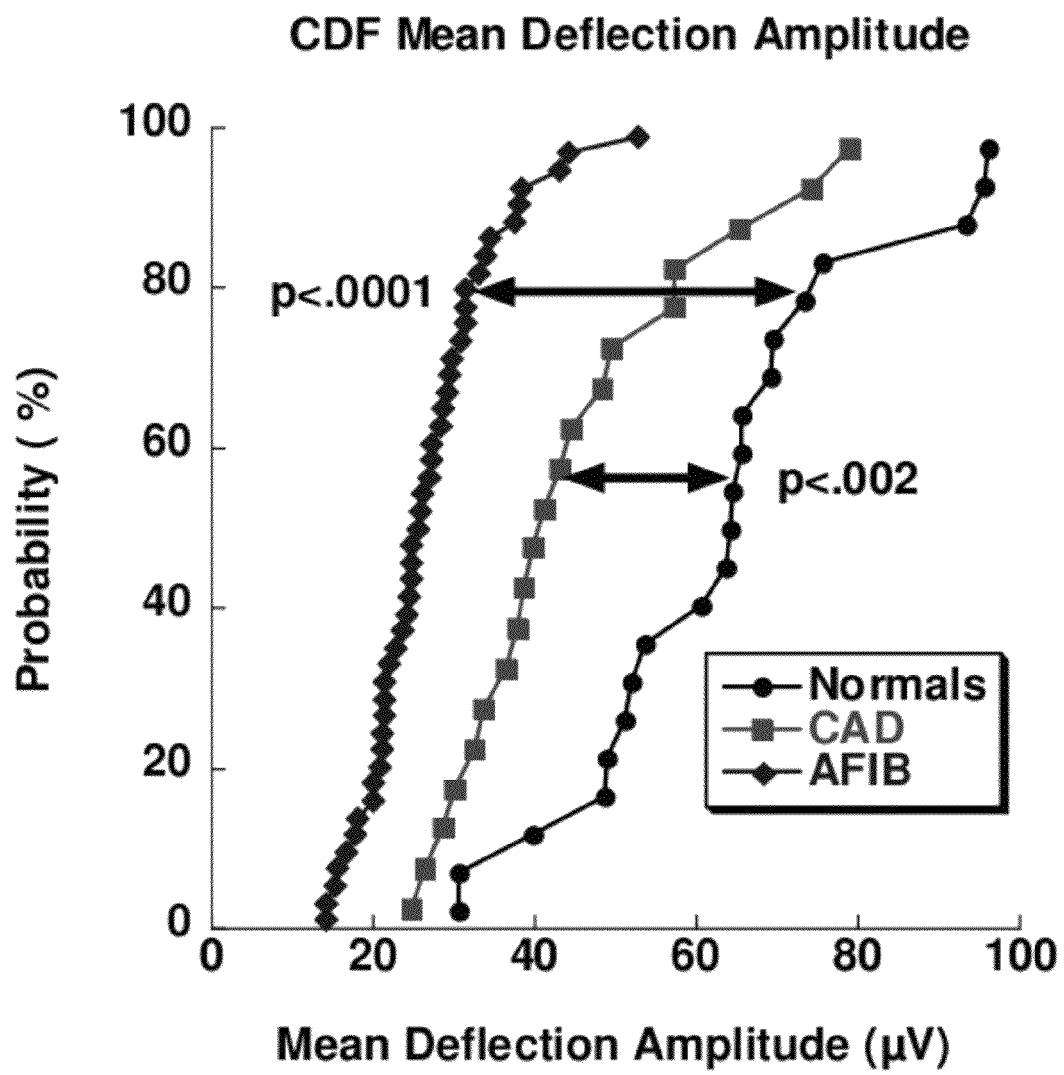
FIG. 4B shows cumulative distribution functions for mean deflection amplitude for the three groups of subjects.

FIG. 4B shows cumulative distribution functions for mean deflection amplitude for the three groups of subjects in FIG. 4A. In this example, the mean deflection amplitude was computed for the significant deflections in the P waves. As shown in FIG. 4B, the subjects with coronary artery disease tend to have a much smaller mean deflection amplitude than the normal subjects, and the subjects with atrial fibrillation tend to have an even smaller mean deflection amplitude than the normal subjects. This is to be expected, since the jagged nature of the signal averaged ECG for a subject with coronary artery disease tends to produce a large number of small deflections, as shown in the example in FIG. 2B.

A Kolmogorov-Smirnov test was performed on the cumulative distribution functions in FIG. 4B. In FIG. 4B, the p-value between the cumulative distribution functions for the subjects with coronary artery disease and the normal subjects was less than 0.002, indicating that the difference in the cumulative distribution functions was due to the underlying discontinuous conduction in subjects with coronary artery disease rather than due to chance. The p-value between the cumulative distribution functions for the subjects with atrial fibrillation and the normal subjects was less than 0.0001.

Figure 4C:
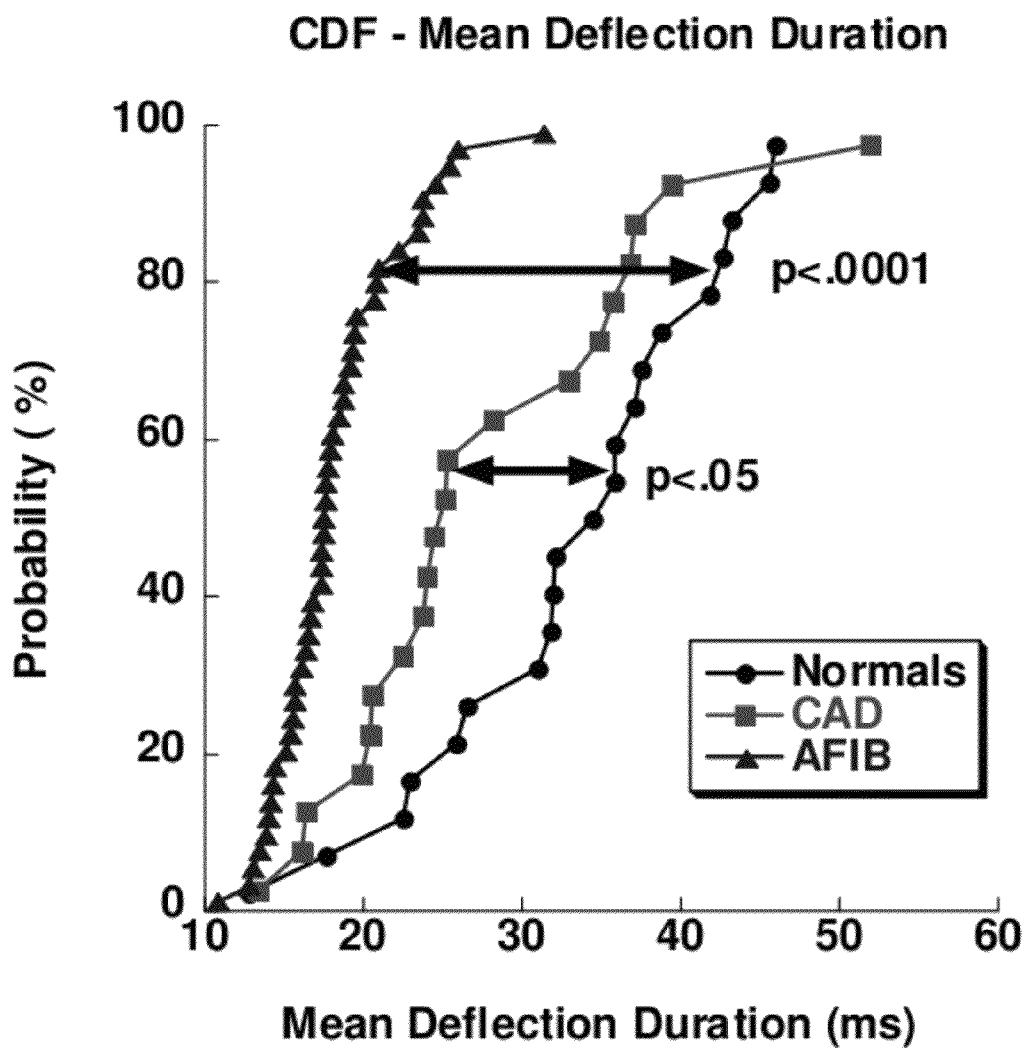
FIG. 4C shows cumulative distribution functions for mean deflection duration for the three groups of subjects.

FIG. 4C shows cumulative distribution functions for mean deflection duration for the three groups of subjects in FIG. 4A. In this example, the mean deflection duration was computed for the significant deflections in the P waves. As shown in FIG. 4C, the subjects with coronary artery disease tend to have a much smaller mean deflection duration than the normal subjects, and the subjects with atrial fibrillation tend to have an even smaller mean deflection duration than the normal subjects. This is to be expected, since the high frequency, jagged nature of the signal averaged ECG for a subject with coronary artery disease tends to produce a large number of small deflections, as shown in the example in FIG. 2B.

A Kolmogorov-Smirnov test was performed on the cumulative distribution functions in FIG. 4C. In FIG. 4C, the p-value between the cumulative distribution functions for the subjects with coronary artery disease and the normal subjects was less than 0.05, indicating that the difference in the cumulative distribution functions was due to the underlying discontinuous conduction in subjects with coronary artery disease rather than due to chance. The p-value between the cumulative distribution functions for the subjects with atrial fibrillation and the normal subjects was less than 0.0001.

Thus, the experimental results in FIGS. 4A through 4C confirm that the signal averaged P waves of a patient with coronary artery disease exhibit fractionation due to discontinuous conduction in the artia, which is a significant contributing factor for atrial arrhythmias. Therefore, a patient's risk for atrial arrhythmia may be accessed by quantifying fractionation in the signal averaged P waves for the patient and normal healthy subjects, and comparing the quantified fractionation for the patient with the quantified fractionation for the normal healthy subjects. The fractionation may be quantified by determining the characteristics of significant deflections, as discussed above. For example, a patient with a large number of small-amplitude short-duration deflections may be at higher risk of arrhythmia, and a patient with a small number of large-amplitude long-duration deflections may be at lower risk of arrhythmia. Although P waves were analyzed in the example above, it is to be appreciated that the analysis is not limited to this example, and that fractionation in signal averaged QRS complexes may be analyzed to access a patient's risk of ventricular arrhythmia in a similar manner.

Figure 5:
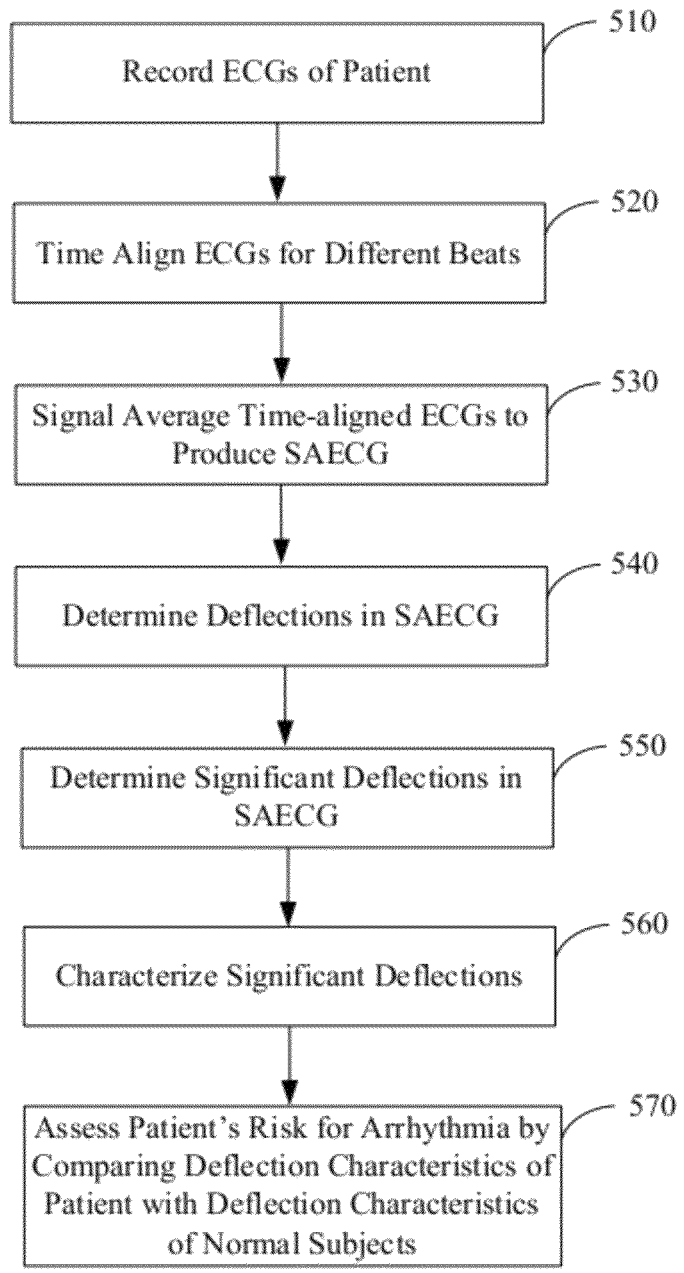
FIG. 5 is a flow chart of a method for assessing cardiac conduction according to an embodiment of the subject technology.

A method for analyzing SAECG signals to assess cardiac conduction is described below with reference to FIG. 5 according to an embodiment of the subject technology.

In step 510, ECGs are recorded for the patient. For example, digital, high resolution (e.g., 16 bit, 1000 Hz sample rate, 0.05-200 Hz bandwidth) ECGs can be recorded over a period of five to ten minutes.

In step 520, the ECGs for different heart beats are time aligned for signal averaging. This may be done by detecting each heart beat, and time aligning each ECG corresponding to a beat by cross correlating the ECG or a portion of the ECG with the ECG or a portion of the ECG of a "template beat" and shifting the ECG over a range of samples until the cross correlation is maximized. If the cross correlation is below a certain amount (e.g., less than 0.98), then the corresponding ECG may be discarded from the signal averaging.

In step 530, the time-aligned ECGs are averaged to produce a signal averaged ECG (SAECG). For example, all the time-aligned ECGs having high correlation (e.g., r>0.98) with the "template beat" may be averaged.

In step 540, deflections in the SAECG are determined. For example, the onset of the P wave in the SAECG may be identified and all local maxima and minima throughout the P-QRS-T segment of the SAECG may be determined. The deflections may then be defined as lines between adjacent local maxima and minima.

In step 550, significant deflections are determined. For example, each deflection that is equal to or exceeds a deflection amplitude threshold may be determined to be a significant deflection. The threshold may be based on a fixed value (e.g., 2 µV) or based on a factor times the maximum deflection occurring in the T-P or P-R segments (e.g., ECG intervals during which there is no ventricular or atrial depolarization).

In step 560, the significant deflections are characterized. For example, all the significant deflections during the P wave in the SAECG may be characterized for an atrial assessment. In another example, all the significant deflections during the QRS complex in the SAECG may be characterized for a ventricular assessment. The characteristics of the significant deflections may include the number of significant deflections, the mean amplitude of the significant deflections and/or the mean duration of the significant deflections.

In step 570, the patient's cardiac conduction is assessed by comparing the deflection characteristics for the patient with the deflection characteristics for normal subjects. For example, a patient with a large number of small-amplitude short-duration deflections compared to normal subjects may be at higher risk of arrhythmia. The deflection characteristics for each normal subject may be determined by performing steps 510-560 for each subject. Further, a SAECG may be determined for each of a plurality of leads and the deflection characteristics may be determined for one or all of the SAECGs for one or all of the leads.

FIG. 6 shows a conceptual block diagram of a system according to an embodiment of the subject technology for obtaining and processing electrocardiographic signals of a patient to assess abnormal electrical conduction in the heart and the patient's risk of arrhythmia. The system comprises a plurality of electrodes 610 which may be placed on the patient's skin (e.g., chest) to measure the electrical activity of the heart. For example, the system may be configured to record standard 12-lead ECGs, where each lead may refer to an individual electrode or an electrode pair.

The system further comprises a processor 655 configured to digitize the electrical signals from the electrodes 610 and process the digital electrical signals into high resolution (e.g., 16 bit, 1000 Hz sample rate, 0.05-200 Hz bandwidth) ECGs. The processor 655 may then time align the ECGs for each lead recorded over multiple heart beats (e.g., five to ten minutes) and average the ECGs to produce a signal averaged ECG (SAECG) for the lead. The processor 655 may then determine significant deflections in one or all of the SAECGs and characterize the significant deflections (e.g., number, mean amplitude and mean duration of the significant deflections). The processor 655 may then compare the deflection characteristics for the patient to deflection characteristics for normal subjects, which may be archived and retrieved from a memory 660. The processor 655 may then assess the patient's risk of arrhythmia based on the comparison and/or display the comparison to a physician (cardiologist) for a risk assessment by the physician. For example, the processor 655 may implement the method in FIG. 5.

The system also includes a display 665 for displaying information to a physician (cardiologist). For example, the processor 655 may output ECGs and SAECGs to the display 665 for display to the physician. The processor 655 may also output the deflection characteristics (e.g., number, mean amplitude and mean duration of the significant deflections) for the patient to the display 665 for display to the physician. The processor 655 may also output corresponding deflection characteristics for normal subjects to the display 665 for comparison.

The processor 655 may perform the various functions described herein by executing instructions stored in memory 660, which may include memory internal to the processor (e.g., cache memory) and/or memory external to the processor (e.g., DRAM, hard drive, etc.). The processor may include a microcontroller, a Digital Signal Processor (DSP), an Application Specific Integrated Circuit (ASIC), a Field Programmable Gate Array (FPGA), hard-wired logic, analog circuitry and/or any combination thereof.

Thus, embodiments of the subject technology provide systems and methods for processing electrocardiographic signals to provide physicians (cardiologists) with a means to assess abnormal electrical conduction in the heart, an established marker of arrhythmia risk. Embodiments of the subject technology may be applied to the P wave to assess conduction in the atria and/or applied to the QRS complex to assess conduction in the ventricles. As discussed above, in young healthy subjects, P waves are generally smooth with only a few large deflections. In patients with coronary disease and those at risk for atrial fibrillation or flutter, the P waves have many, small deflections that are markers of the underlying discontinuous conduction, an arrhythmogenic substrate known to increase arrhythmia risk.

In one embodiment, signal averaging of time-aligned P waves is performed to achieve improved signal-to-noise ratio (SNR). Significant deflections in the signal averaged P waves are then determined, where the level of significance may be established by using noise levels specific to each ECG signal. The number and characteristics (e.g., mean amplitude and mean duration) of the significant deflections are then determined and used to assess the patient's risk of arrhythmia. The arrhythmia risk assessment may be based on the assumption that high risk is associated with many small deflections (as confirmed by observed fractionation of electrical activity observed in experimental or clinical electrophysiology labs in patients with coronary disease or known risk) and that low risk is associated with a small number of large deflections.

Current methods for atrial assessment and AF ablation require expensive, high risk, long duration procedures in hospital operating rooms (EP labs) and experimental MRI imaging techniques to detect and assess abnormal conduction and risk. Related technology for assessing ventricular conduction abnormalities ("late potential detection") is called signal averaged ECG (SAECG) which is inexpensive and low risk but addresses only one part of ventricular abnormality. Moreover, conventional late potential SAECG uses a frequency analysis based approach and extensive filtering whereas embodiments of the subject technology use a simple wave detection and classification approach operating on the raw unfiltered signal averaged signals.

Embodiments of the subject technology allow rapid, inexpensive, noninvasive (no risk) assessment as a screening and assessment tool. In one embodiment, all that may be required is continuous, high resolution (16 bit, 1000 Hz sample rate) ECG recording from 12-15 leads and computer processing of the signals to assess the arrhythmogenic substrate for either the atria or ventricles.

Embodiments of the subject technology may also be used to assess the effectiveness of AF therapies. For example, the characteristics (e.g., number, mean amplitude and mean duration) of the significant deflections for a patient may be determined before and/or after AF therapy. In this example, the AF therapy may be determined to be effective if the number of significant deflections is reduced, the mean amplitude of the significant deflections increases and/or the mean duration of the significant deflections increases, which may be indicative of smoother conduction in the heart. The ability to assess the effectiveness of AF therapies may be used to stratify patients with history of AF into high/low benefit groups relative to success/failure of AF therapies (ablation versus medical) or even likelihood of success/failure of repeat ablation.

Thus, embodiments of the subject technology may be used to a) identify patients potentially at risk of developing AF, b) stratify patients already in AF into treatment groups (ablation versus medical therapies), and c) stratify patients who have already been ablated into additional ablation versus medical therapy groups. Early identification of those at risk of acquiring AF encourages preventative measures in these patients. Given the high rate of failure of ablation therapy, a means to identify those unlikely to benefit from repeat ablation would reduce the cost and risk of unnecessary procedures.

Embodiments of the subject technology may be used to assess a patient's risk for various types of atrial arrhythmias and ventricular arrhythmias including atrial fibrillation, ventricular fibrillation, atrial tachycardia, ventricular tachycardia, and other types of arrhythmias.

Although preferred embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A method of estimating a risk of a future arrhythmia in a patient, comprising:
    receiving electrocardiographic signals of the patient over a plurality of heart beats;
    averaging the electrocardiographic signals to produce an averaged electrocardiographic signal;
    determining a plurality of deflections in the averaged electrocardiographic signal, wherein each deflection comprises a segment between adjacent extrema in the averaged electrocardiographic signal;
    determining a plurality of significant deflections from the determined plurality of deflections, wherein each significant deflection has an amplitude exceeding a threshold; and
    estimating a risk of a future arrhythmia in the patient based on determined number of the significant deflections within a portion of the averaged electrocardiographic signal.

2. The method of claim 1, wherein the estimating is further based on determined amplitudes of the significant deflections within the portion.

3. The method of claim 2, wherein the threshold comprises a factor times the maximum deflection amplitude in at least one of a T-P, a P-R, or an S-T segment of the averaged electrocardiographic signal.

4. The method of claim 2, wherein the estimating is based on a mean amplitude of the significant deflections.

5. The method of claim 1, wherein the estimating is based on the determined number, determined amplitudes, and determined durations of the significant deflections within the portion.

6. The method of claim 1, wherein the portion comprises a P wave of the averaged electrocardiographic signal.

7. The method of claim 6, wherein the estimating comprises:
    comparing the determined number, a mean amplitude, and a mean duration of the significant deflections of the patient to a respective number, a respective mean amplitude, and a respective mean duration of significant deflections of at least one normal subject; and estimating a risk of atrial fibrillation in the patient based on the comparison.

8. The method of claim 1, wherein the portion consists essentially of a P wave of the averaged electrocardiographic signal.

9. The method of claim 1, wherein the portion of the averaged electrocardiographic signal comprises a QRS complex, and the estimating comprises estimating a risk of ventricular arrhythmia of the patient.

10. The method of claim 9, wherein the estimating comprises:
  comparing the determined number of the significant deflections of the patient to a respective number of significant deflections of at least one normal subject; and
  estimating a risk of at least one of ventricular tachycardia or ventricular fibrillation in the patient based on the comparison.

11. The method of claim 1, wherein the estimating is further based on determined durations of the significant deflection within the portion.

12. The method of claim 11, wherein the estimating is based on a mean duration of the significant deflections.

13. The method of claim 1, wherein the plurality of significant deflections are contiguous within the portion of the averaged electrocardiographic signal.

14. A system for estimating a risk of arrhythmia in a patient, comprising:
  a processor configured to receive electrocardiographic signals of the patient over a plurality of heart beats; to average the electrocardiographic signals to produce an averaged electrocardiographic signal; to determine a plurality of deflections in the averaged electrocardiographic signal, wherein each deflection comprises a segment between adjacent extrema in the averaged electrocardiographic signal; to determine a plurality of significant deflections from the determined plurality of deflections, wherein each significant deflection has an amplitude exceeding a threshold; and to estimate a risk of a future arrhythmia in the patient based on a determined number of the significant deflections within a portion of the averaged electrocardiographic signal.

15. The system of claim 14, wherein the processor is configured to estimate the risk of arrhythmia further based on determined amplitudes of the significant deflections within the portion.

16. The system of claim 14, wherein the processor is configured to estimate the risk of arrhythmia based on the determined number, determined amplitudes, and determined durations of the significant deflections within the portion.

17. The system of claim 14, wherein the portion comprises a P wave of the averaged electrocardiographic signal.

18. The system of claim 14, wherein the portion consists essentially of a P wave of the averaged electrocardiographic signal.

19. The system of claim 18, wherein the processor is configured to the estimate the risk of arrhythmia by:
  comparing the determined number, a mean amplitude, and a mean duration of the significant deflections of the patient to a respective number, a respective mean amplitude, and a respective mean duration of significant deflections of at least one normal subject; and
  estimating a risk of atrial fibrillation in the patient based on the comparison.

20. The system of claim 14 wherein the portion of the averaged electrocardiographic signal comprises a QRS complex.

21. The system of claim 20, wherein the processor is configured to estimate the risk of arrhythmia by:
  comparing the determined number of the significant deflections of the patient to respective number of significant deflections of at least one normal subject; and
  estimating a risk of at least one of ventricular tachycardia or ventricular fibrillation in the patient based on the comparison.

22. The system of claim 14, wherein the process or is configured to estimate the risk of arrhythmia further based on determined durations of the significant deflections within the portion.

23. The system of claim 14, wherein the plurality of significant deflections are contiguous within the portion of the averaged electrocardiographic signal.

* * * * *

UNITED STATES PATENT AND TRADEMARK OFFICE
CERTIFICATE OF CORRECTION

| | | |
|---|---|---|
| PATENT NO. | : 8,437,839 B2 | Page 1 of 1 |
| APPLICATION NO. | : 13/085444 | |
| DATED | : May 7, 2013 | |
| INVENTOR(S) | : Robert L. Lux | |

It is certified that error appears in the above-identified patent and that said Letters Patent is hereby corrected as shown below:

In the Specification:

In column 1: Add the following paragraph in the application after the title:

--Government License Rights

This invention was made with government support under grant number P50 HL052338 awarded by the National Institutes of Health. The government has certain rights in the invention.--

Signed and Sealed this
Thirtieth Day of June, 2015

Michelle K. Lee
*Director of the United States Patent and Trademark Office*